United States Patent [19]
Zini et al.

[11] Patent Number: 6,143,797
[45] Date of Patent: Nov. 7, 2000

[54] USE OF SODIUM 2-MERCAPTOETHANESULFONATE IN SURGERY

[75] Inventors: Carlo Zini; Salvatore Bacciu; Angelo Gandolfi; Fabio Piazza; Enrico Pasanisi, all of Parma, Italy

[73] Assignee: A.R.D.O. (Associazione Ricerca e Didattica in Otologia, Parma, Italy

[21] Appl. No.: 09/284,195

[22] PCT Filed: Oct. 7, 1997

[86] PCT No.: PCT/EP97/05485

§ 371 Date: Jun. 9, 1999

§ 102(e) Date: Jun. 9, 1999

[87] PCT Pub. No.: WO98/16213

PCT Pub. Date: Apr. 23, 1998

[30] Foreign Application Priority Data

Nov. 10, 1996 [IT] Italy ................................. MI96A2117

[51] Int. Cl.⁷ .................................................... A61K 31/10
[52] U.S. Cl. ............................................................. 514/709
[58] Field of Search ............................................... 514/709

[56] References Cited

U.S. PATENT DOCUMENTS 5,244,920  9/1993  Reiner et al. ............................ 514/554
5,661,188  8/1997  Weissman et al. .

FOREIGN PATENT DOCUMENTS 334 083    9/1989  European Pat. Off. .
0 591 710  4/1994  European Pat. Off. .

OTHER PUBLICATIONS

Ziccardi et al. (Nuclear dacryoscintigraphy: its role in oral and maxillofacial surgery), Oral surgery . . . , vol. 80/6, pp. 645–649, (Dec. 1995).

Madwed et al (Mucocele of the appendix . . . ), AJR. American J. of Roentgenology, vol. 159/1, pp. 69–72, (1992).

Chiossone E. (Preventive tympanoplasty in children: . . . ), Revue de Laryngologie . . . , vol. 116/2, pp. (137–139), (1995).

Tay L.: "effect of mesna during the first 72 hours after abdominal surgery" Excerpta Medica, vol. 490, 1979, p. 105 XP002050280 see the whole document.

Verzar F.: "mesna for postoperative treatment after nasal surgery" Therapiewochi, vol. 29, No. 18, 1979, pp. 3224–3225 XP002050281 see p. 3224; table 1.

Skondia V.: "introducing mesna" Excerpta Medica, vol. 490, 1979, p. 102 XP002050282 see the whole document.

Brown et al.: "drugs affecting clearance of middle ear secretions" Ann. Oto. Rhinol. Laryngol., vol. 94, No. 211, 1985, pp. 3–15, XP002050283 see p. 4, right–hand column, paragraph 2 see page 7, right–hand column, paragraph 2.

*Primary Examiner*—William R. A. Jarvis
*Assistant Examiner*—Vickie Kim
*Attorney, Agent, or Firm*—Nixon & Vanderhye

[57] ABSTRACT

Methods of facilitating detaching pathological tissues from healthy tissues with which they have formed adherences and facilitating detachment of healthy tissues from other healthy tissues such as in plastic surgery are described in which an effective amount of sodium 2-mercaptoethanesulfonate (MESNA) is applied to the tissue or tissues.

9 Claims, No Drawings

USE OF SODIUM 2-MERCAPTOETHANESULFONATE IN SURGERY

This application is a 35 U.S.C. §371 of PCT/EP97/05485 filed Oct. 7, 1997.

The present invention refers to topical pharmaceutical formulations containing sodium 2-mercaptoethanesulfonate (MESNA), the use of MESNA for the preparation of pharmaceutical formulations intended to be used in surgical procedures that involve the dissection of tissues and the use of MESNA in said surgical procedures.

One of the fundamental principles of surgery performed on all parts of the human body consists in detaching the various pathological tissues from the healthy tissues with which they have formed adherences. Furthermore, in most cases during the surgical approaches, even healthy tissues need to be detached from each other in order to penetrate deep through the cutaneous layers.

At present, such detachment is performed only with mechanical instruments separating the adherent surfaces using "dissectors", stripping therefore adherences between the two surfaces or cutting them with the bisturi or scissors.

The detachment of tissues according to the present method can be quite tedious and is often responsible for long surgical operations. An important technical progress in this field would be to facilitate the detachment of tissues, thereby reducing operation duration, the medical cost of such operations, as well as health risks for the patient.

Sodium 2-mercaptoethanesulfonate (hereinafter referred to as MESNA), is included in a class of thiolic drugs which produce mucolysis by breaking the disulfur bridges of the polipeptide chains of mucus.

Up to now MESNA was present in the market as topical aerosol, nasal spray and intravenous formulations. The registered indications include the treatment of pathologies of the respiratory system such as chronic bronchitis, bronchitis with asthma, asthma, bronchoconstriction, emphysema, bronchiectasis and mucoviscidosis, rhinitis and chronic pharyngolaringitis.

During the post operative phase, MESNA is moreover used together with respiratory physiotherapy, to facilitate expectoration and as coadjuvant in the prevention of pulmonary complications due to obstructive bronchial phenomena. It is also useful in pulmonary atelectasies due to bronchial occlusion.

Moreover in the oncological field MESNA is used to prevent toxic lesions of the urinary tract by antineoplastic agents such as oxazaphosphorines/cyclo-phosphamide, iphosphamide).

We have now surprisingly found that MESNA facilitates the dissection of tissues during surgery when applied in the form of a topical formulation on the tissues to be dissected.

Thus, the present invention provides topical formulations, preferably sterile solutions or powders, which can be directly applied during surgical procedure on the tissues in order to facilitate their dissection.

More specifically, such formulations may be in the form of sterile solutions at concentrations of MESNA ranging from 1 to 50% by weight, preferably 10–20% by weight, or dispersive powders. The dosage of the formulations is not limited by side-effects due to the optimal tolerability of MESNA when it is applied directly to tissues.

The formulations of the invention can be used in any surgical procedure where the dissection of the various tissue layers is necessary.

The invention is particularly useful in E.N.T. (Ears, Nose and Throat) surgery during which frequently difficult cases can be encountered.

One of these surgical indication is the removal of cholesteatoma.

The topical formulations containing MESNA facilitate removal of the "glue" in otitis media with effusion and facilitate the removal of cholesteatoma debris pre, intra and post operatively (in the case of recurrent cholesteatoma). The topical formulations of the invention allow the chemically assisted dissection (CADISS) of the matrix of the cholesteatoma in the mastoid, epitympanum and posterior mesotympanum. Moreover, they facilitate the dissection of the matrix from the oval and round windows, from the bones of the inner ear and particularly from the stapes and from the facial nerve. During second stage procedures in tympanoplasty, they allow to rapidly remove the connectival covering which surrounds the silastic (plastic sheet placed in the middle ear for drainage) and to remove residual cysts (residual cholesteatoma).

Topical formulations of the invention containing MESNA facilitate the removal of granulomatous inflammation tissue around the cholesteatoma matrix.

Another special indication is the treatment of fistulae and invasions of the labyrinth because said formulations allow the dissection of the matrix of the cholesteatoma without damaging the labyrinth.

In the surgery of meningeal and meningoencephalic hernias, the topical formulations of the invention allow an easy dissection of the dura mater from the bone and from the normal and pathological tissues of the middle ear. Other applications in the field of otological surgery are represented by surgery of tympanic glomus tumors, tympanosclerosis and cholesterol granulomas. The topical formulations of the invention may be employed even in cases of sudden hearing loss.

The topical formulations of the inventon may be used also in the otoneurosurgical field, for example to facilitate removal of acoustic neuromas, of glomus tumors, of meningiomas and all tumors of the skull base. In particular said formulations facilitate the maintenance of a good cleavage plane between the tumor and the cranial nerves and between the tumor and arteries and veins and between the tumor and the important structures of the central nervous system (brain, cerebellum, brain stem).

In nasal surgery, topical formulations of the invention are useful for the flushing of the paranasal synuses in endoscopic surgery. They allow the rapid removal of blood clots, the dissection of pathological tissues from anatomical structures. In plastic surgery of the nasal septum they facilitate the dissection of the mucosa from the deformed osteocartilagenous parts of the septum (both in first and secondary procedures).

During rhinoplastic surgery the topical formulations of the invention containing MESNA can facilitate the dissection of the periostium before performing lateral and medial osteotomy or other corrective manouvers such as that of the nose bone. The trans-septal surgery of the sphenoid bone is another indication for the use of said topical formulations which can be administered through special dissectors (during the approach) and through special curettes (for the removal of the tumoral mass).

In salivary glands surgery, the topical formulations of the invention containing MESNA allow the enucleation of the tumoral mass, after having found its capsule which can be traced by special equipment, allowing an easier dissection of the facial nerve from the salivary gland tissue and from the walls of the parotid compartment.

In the surgery of the oral and oropharyngeal cavity, the topical formulations of the invention facilitate the dissection of gums from teeth before extraction, and facilitate the detachment of soft tissues from the palate during transpalatine procedure, facilitate tonsillectomy by dissection, etc.

In neck surgery the topical formulations of the invention are useful in the surgery of the thyroid and parathyroid glands, in partial or total laryngectomies, in enlarged pharyngectomies, in neck dissection, in tracheotomy, etc.

The formulations of the invention may also be used in other fields of surgery such as:

Neurosurgery: for the dissection of the dura from the cranial bones, of the endocranial benign and malignant tumors from normal brain tissues and blood vessels, for an easier maintenance of an optimal plane of cleavage between the tumor and neural and vascular structures, etc.

Maxillo-facial surgery: to facilitate the different transfacial and transnasal approaches and the dissection of normal tissues and pathological tissues, such as nasopharingeal angiofibroma and tumors of the paranasal sinuses, etc.

Vascular surgery: to facilitate the endovascular dissection of thrombi, administering the drug through special catheters, of within the open vessels using special dissecting equipment, and to facilitate dissection at aortic or abdominal aneurysms and surgery of varicose veins, etc.

General surgery: to facilitate the detachment of abdominal viscera which have adherences between themselves and the abdominal walls and to facilitate colecystectomy, appendectomy, other abdominal surgical procedures, etc.

In urology: to facilitate the treatment of renal and urethral calculi, during endoscopic and trans-abdominal surgery of the bladder and prostate, to facilitate exeresis of bladder or kidney tumors and during surgical treatment of venal malformations, etc.

Orthopedics: in arthroscopic procedures and in the treatment of herniated disk, arthroplasty, tumor surgery, etc.

Plastic surgery to facilitate the removal of sebaceous cysts, to allow an easier face lifting and the dissection of the different tissue layers, mostly during surgical revisions, functional and aesthetic rhynoplasty, mammoplasty, etc.

Ophthalmology: to facilitate the dissection during crystalline lens surgery.

Gynaecology: to facilitate the dissection of normal and pathological tissues, during laparotomic myomectomies, conservative treatment for pelvic endometriosis, vaginal hysterectomy, etc., respecting the anatomical planes and reducing post-operative complications such as inflammatory reactions, fibrosis and adhesions.

Skull base surgery: to facilitate removal of glomus tumors of meningiomas and all tumors of the skull base. MESNA helps to maintain a good cleavage plane between the tumor and the cranial nerves, arteries, veins and the central nervous system (brain, cerebellum, brainstem), etc.

Thoracic surgery: to facilitate excision of tumors of the lungs, mediastinum, etc. and to loosen pleural adherences (also during thoracoscopy).

Cardiovascular surgery: to facilitate surgical approach to the heart and to the aorta, etc., to favor an easier detachment of the pericardium to loosen adherences (especially during second procedures), etc.

Dentistry: to facilitate the detachment of the gums, the surgical removal of an impacted lower third molar, etc.

In the following examples, which illustrate the invention without however limiting it, the percentages are expressed by weight.

EXAMPLES

1) In vitro Experiments

A cholesteatoma from surgical procedure was divided in equal parts of 25 g (dry weight). The material was then placed in test tubes containing 5 ml of each of the testing solutions in physiological saline:
a) Test tube n. 1: acetylcysteine (20%)
b) Test tube n. 2: chymotrypsin (1%)
c) Test tube n. 3: MESNA (20%)
d) Test tube n. 4: MESNA (10%)

The samples were left at 37° C. and the dissolution time of cholesteatoma parts was evaluated. While acetylcysteine and chymotrypsin have demonstrated a weak dissolving effect on the cholesteatoma, the 10% and 20% MESNA solutions, resulted in an optimal and rapid effect.

2) MESNA was moreover experimented on 3 fresh dog cadavers. (Beagle; weight: 10 Kg). MESNA (10 ml of a solution at 20%) was administered to about 10 $cm^2$ of connective tissue layers. After 5 minutes, the dissection of tissue layers turned out to be easier with respect to untreated control tissues. In particular, the force required for the dissection was considerably lower and dissected layers showed neater borders without wrinkles or tears.

3) The drug was also employed in man to facilitate the removal of ear wax from the auditory canal. There was no evidence of allergic or inflammatory reactions. 3–4 ml of a 10% solution were instilled in the patient's ear.

4) The drug was lastly employed intraoperatively (10 consenting adult subjects with chronic otitis media with cholesteatoma) using the same 10% MESNA solution. With respect to untreated control cases affected by comparable pathology, the removal of the cholesteatoma debris, the dissection of the matrix and of the granulation tissue resulted facilitated. No inflammatory reactions nor ototoxicity was observed.

5) Topical formulations containing MESNA have been used also to facilitate surgical operations in the non-E.N.T. fields. For example, the drug has been used in the maxillo-facial field to facilitate sublabial approach for the resection of the nasal and paranasal sinus. This technique allows to expose the structures of the facial third medium, avoiding any cutaneous incisions. This operation provides a sublabial incision. Thanks to the use of MESNA, the periosteum, in the anterior part of the maxilla, is lifted bilaterally together with the soft tissues more easily, thus reducing the risk of damaging the infraorbital nerves.

After having carried out the usual inter-cartilaginous incisions, typical of the rhynoplastic surgery, using suitable instruments for the chemically assisted dissection (CADISS), the soft nasal tissues are separated from the nasal osteo-cartilaginous skeleton. Thanks to a series of incisions, the skeletonized nose is linked to the anterior maxillary area, which have already been detached.

Then, the skin of the facial medium third undergoes a complete detachment by suitable smooth instruments for the chemically assisted dissection, and it is brought to the frontonasal suture line and to the infraorbital rima, as well as laterally, up to the zygomatic process. At this point, it is possible to obtain a suitable access to the nasal cavities and to the paranasal sinus, using the usual techniques for the exeresis of both benign and malignant tumors.

6) MESNA facilitates the detachment of tumoral lesions.

When a digital detachment of the lesion is provided, a topical formulation containing MESNA is instilled in the surgical field by way of a system of irrigation, which is usually regulated by the assistant.

Among the most frequent post-surgical adverse effects, there is the recurrent formation of crusts in the nasal cavities. The intranasal cavities show a positive response to the topical application of MESNA.

The quantity of formulation applied on the surgical field can vary greatly in accordance to the chosen procedure. In the microscopical applications the doses are usually inferior to those used in standard therapy. In the macroscopical field the quantities can be superior. Systems for the removal of excess topical formulation containing MESNA can be employed, such as suction, adsorbent gauze so as to limit systemic absorption.

Generally the quantities vary from 1 ml to 10 ml of a solution at 10–20%.

What is claimed is:

1. A method of facilitating detachment of healthy tissues from each other, said method comprising applying to said tissue or tissues an effective amount of sodium 2-mercaptoethanesulfonate.

2. A method of facilitating detachment of tissues during a surgical procedure which method comprises applying to said tissue an effective amount of a solution of sodium 2-mercaptoethanesulfonate to the tissues.

3. A method of using sodium 2-mercaptoethanesulfonate in a surgical procedure that involves the dissection of tissues, said method comprising administering to the tissues of a patient in need of same an effective amount of sodium 2-mercaptoethanesulfonate.

4. A method of facilitating the detachment of tumoral tissues, said method comprising applying to said tissue an effective amount of sodium 2-mercaptoethanesulfonate.

5. A method according to claim 3, wherein said surgical procedure is selected from the group consisting of surgical procedures involving the removal of cholesteatoma or cholesteatoma debris pre-, intra- and post-operatively.

6. A method according to claim 3, wherein said surgical procedure is selected from the group consisting of neck surgery, neurosurgery, maxillo-facial surgery, vascular surgery, general surgery, urological surgery, orthopedic surgery, plastic surgery, ophthalmic surgery, gynecology, skull base surgery, thoracic surgery, cardiovascular surgery and dentistry.

7. A method according to claim 6, wherein the effective amount of sodium 2-mercaptoethanesulfonate is applied directly during surgical procedure on the involved tissues.

8. A method according to claim 4, wherein said surgical procedure is selected from the group consisting of surgical procedures involving the removal of cholesteatoma or cholesteatoma debris pre-, intra- and post-operatively.

9. A method according to claim 4, wherein said surgical procedure is selected from the group consisting of neck surgery, neurosurgery, maxillo-facial surgery, vascular surgery, general surgery, urological surgery, orthopedic surgery, plastic surgery, ophthalmic surgery, gynecology, skull base surgery, thoracic surgery, cardiovascular surgery and dentistry.

* * * * *